(12) United States Patent
Kaldor et al.

(10) Patent No.: US 7,195,752 B2
(45) Date of Patent: Mar. 27, 2007

(54) SURFACTANT COMPOUNDS AND USES THEREOF

(75) Inventors: Istvan Kaldor, Durham, NC (US); Brian Edgar Looker, Stevenage (GB); Christopher James Lunniss, Stevenage (GB); Alison Judith Redgrave, Stevenage (GB)

(73) Assignee: Glaxo Group Limited, Greenford (GB)

( * ) Notice: Subject to any disclaimer, the term of this patent is extended or adjusted under 35 U.S.C. 154(b) by 224 days.

(21) Appl. No.: 10/485,595

(22) PCT Filed: Aug. 2, 2002

(86) PCT No.: PCT/GB02/03586

§ 371 (c)(1),
(2), (4) Date: Feb. 2, 2004

(87) PCT Pub. No.: WO03/013610

PCT Pub. Date: Feb. 20, 2003

(65) Prior Publication Data

US 2004/0234556 A1 Nov. 25, 2004

(30) Foreign Application Priority Data

Aug. 3, 2001 (GB) ................................ 0118994.3
Mar. 23, 2002 (GB) ................................ 0206892.2

(51) Int. Cl.
*A61K 9/12* (2006.01)
*A61K 9/14* (2006.01)
*A61K 31/05* (2006.01)
*A61K 31/56* (2006.01)
*A61K 47/00* (2006.01)
*A61K 47/06* (2006.01)
*C07C 59/00* (2006.01)

(52) U.S. Cl. ........................................ 424/45; 562/586
(58) Field of Classification Search ................ 424/45; 562/12, 586
See application file for complete search history.

(56) References Cited

U.S. PATENT DOCUMENTS

| 3,250,808 | A | | 5/1966 | Moore, Jr. et al. |
| 3,498,923 | A | | 3/1970 | Bernett et al. |
| 5,849,265 | A | * | 12/1998 | Li-Bovet et al. ............... 424/45 |
| 2001/0046474 | A1 | * | 11/2001 | Weers et al. .................... 424/45 |

FOREIGN PATENT DOCUMENTS

| EP | 0 021 739 A | 1/1981 |
| EP | 02 49975 A | 12/1987 |
| JP | 04 283538 A | 10/1992 |
| JP | 053 31582 A | 12/1993 |
| WO | 91/11173 A | 8/1991 |
| WO | 91 14422 A | 10/1991 |
| WO | 91 14422 A | 10/1991 |
| WO | 92 00107 A | 1/1992 |
| WO | 97/26017 A | 7/1997 |
| WO | 97/30969 A | 8/1997 |
| WO | 99/02193 A | 1/1999 |
| WO | 99/03509 A | 1/1999 |

OTHER PUBLICATIONS

Dickinson, P. A. et al. "An Investigation of the Solubility of Various Compounds in the Hydrofluoroalkane Propellants and Possible Model Liquid Propellants," J. Aerosol. Sci. 2000, 13(3), 179-186.*
Lacy, C.; Armstrong, L. L.; Lipsy, R. J.; Lance, L. L. Drug Information Handbook, Lexi-Comp, Inc.: Cleveland, 1993, pp. 397.*
Weinmayr, V.: "Hydrogen fluoride as a condensing agent. VI Reactions of fluoroolefins with formaldehyde in hydrogen fluoride," J. Org. Chem., vol. 28, 1963, pp. 492-494, XP001183282.
Muller, N.: "Problematic chemical shifts of a fluorine-labeled surfactant and oil in some microemulsions systems," J. Phys. Chem., vol. 86, 1982, pp. 2047-2049, XP002297139.
Muller, N., et. al., "Investigation of micelle structure by fluorine magnetic resonace. I. Sodium 10,10,10-trifluorocaprate and related compounds," J. Phys. Chem., vol. 71, No. 4, Mar. 1967, pp. 957-962 XP002230279.
Gavlin, G., et al.: "The synthesis of omega-trifluorostearic acid and omega-trifluoro-n-octadecyl amine," J. Org. Chem., vol. 21, Dec. 1956, pp. 1342-1347, XP002230280.

(Continued)

*Primary Examiner*—Johann R. Richter
*Assistant Examiner*—James Henry Alstrum-Acevedo
(74) *Attorney, Agent, or Firm*—Alice P. Bradney

(57) ABSTRACT

A pharmaceutical aerosol formulation that includes a particulate medicament, one or more fluorocarbon or hydrogen-containing fluorocarbon propellants and a compound of the general formula (I)

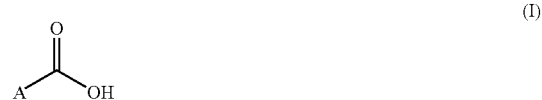

(I)

or a salt or solvate thereof is disclosed, wherein
A represents a straight chain $C_{1-16}$ alkylene substituted by n groups of formula B;
n represents an integer 1 to 3; and
B independently represents $C_{1-4}$ fluoroalkyl$C_{0-6}$ alkylene-, $C_{1-4}$ fluoroalkyl$C_{0-6}$ alkylene-O—, or $C_{1-4}$ alkyl$C_{0-6}$ alkylene-O— wherein at least one substituent of formula B contains at least one fluorine atom and each $C_{1-4}$ fluoroalkyl- moiety contains one or more fluorine atoms but not more than 3 consecutive perfluorinated carbon atoms. Compounds of formula (I) and uses of such compounds are also disclosed.

16 Claims, No Drawings

OTHER PUBLICATIONS

Park, J.D., et al., "Applicability of the Arndt-Eistert reaction to fluorinated acids and their derivatives," J. Org. Chem., vol. 23, Aug. 1958, pp. 1166-1169 XP002230281.

Brace, N.O.: "Long chain alkanoic and alkenoic acids with perfluoroalkyl termial segments," J. Org. Chem., vol. 27, Dec. 1962, pp. 4491-4498 XP001122366.

Gu, C., et al., "Dissociative and reactive hyperthermal ion-surface collisions . . . " J. Am. Chem. Soc. vol. 121, 1999, pp. 10554-10562, XP001135063.

Graupe, M., et. al., "Terminally perfluorinated long-chain alkanethiols" J. Fluorine Chem., vol. 93, No. 2, Feb. 4, 1999 pp. 107-115, XP004156221.

* cited by examiner

SURFACTANT COMPOUNDS AND USES THEREOF

This application is filed pursuant to 35 U.S.C. § 371 as a United States National Phase Application of International Patent Application Serial No. PCT/GB02/03586 filed Aug. 2, 2002, which claims priority from Great Britain Application No. 0118994.3 filed in the United Kingdom on Aug. 3, 2001 and Great Britain Application No. 0206892.2 filed Mar. 23, 2002.

This invention relates to novel surfactants and aerosol formulations thereof for use in the administration of medicaments by inhalation.

The use of aerosols to administer medicaments has been known for several decades. Such aerosols generally comprise the medicament, one or more chlorofluorocarbon propellants and either a surfactant or a co-solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However, these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise fluorocarbons and hydrogen-containing chlorofluorocarbons, and a number of medicinal aerosol formulations using such propellant systems are disclosed in, for example, EP0372777, WO91/04011, WO91/11173, WO91/11495 and WO91/14422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvants such as alcohols, alkanes, dimethyl ether, surfactants (including fluorinated and non-fluorinated surfactants, carboxylic acids, polyethoxylates etc) and even conventional chlorofluorocarbon propellants in small amounts intended to minimise potential ozone damage.

It is essential that the prescribed dose of aerosol medication delivered from the MDI to the patient consistently meets the specifications claimed by the manufacturer and complies with the requirements of the FDA and other regulatory authorities. That is, every dose dispensed from the can must be the same within close tolerances. Therefore, it is important that the formulation be substantially homogenous throughout the administered dose at the time of actuation of the metering valve. It is also important that the concentration of the suspension does not change significantly when stored for a prolonged period.

It is particularly important that the FPM (fine particle mass) of the suspension does not significantly decrease on storage, as the FPM is a measure of the amount of drug from each dose that will reach the therapeutic target in the lung.

In the case of suspension formulations, to control aggregation of fine particles, and thereby influence the dispersability of the suspension it is well established in the art that fluorinated surfactants may be used to stabilise micronised drug suspensions in fluorocarbon propellants such as 1,1,1,2-tetrafluoroethane (P134a) or 1,1,1,2,3,3,3-heptafluoro-n-propane (P227), see for example U.S. Pat Nos. 4,352,789, 5,126,123, 5,376,359, U.S. application Ser. No. 09/580008, WO91/11173, WO91/14422, WO92/00062 and WO96/09816.

WO92/00061 discloses non-fluorinated surfactants for use with fluorocarbon propellants. Certain long chain alkanoic acids with perfluoroalkyl terminal segments including 12,12,13,13,13-pentafluorotridecanoic acid ($CF_3CF_2(CH_2)_{10}COOH$) are disclosed in *J. Org. Chem.* (1962) 27, 4491–4498 (Brace et al). The compounds are said to have surfactant properties in aqueous systems but no mention is made of suitability for use in pressurised aerosol formulations.

Processes for preparing trifluoromethylated organic molecules such as 12,12,12-trifluorododecanoic acid ($CF_3(CH_2)_{10}COOH$) are described in J. Org. Chem. (1984) 49, 2826–2827 (Muller), J. Fluorine Chem. (1999) 93, 107–115 (Graupe et al) and French patent application 2,613,357 (Atochem).

Certain long chain alkanoic acids with a trifluoromethyl terminus including 18,18,18-trifluorooctadecanoic acid and their use in preparing Langmuir-Blodgett films are described in J. Am. Chem. Soc. (1999) 121, 10554–10562 (Gu et al).

Certain fluorinated alkyl and alkoxy acid compounds are disclosed in the following documents:
J. Mol. Struct. 485–486, 373–384,1999 Publisher Elsevier Science;
Application WO 9821177;
Application EP 264080
J. Pharm. Sci., 75(10), 987–91, 1986;
Mitsui Petrochemical Industries Ltd, Japan: JP 58196247;
Application EP 021739;
Daikin Kogyo Co. Ltd, Japan: JP 57018730;
J. Phys. Chem, 86(II), 1982, 2047–9;
J. Fluorine Chem. 12(6), 471–9, 1978;
ACS Symp. Ser., 688(Cellulose Derivatives) 315–331, 1998. Publisher American Chemical Society;
UKR. Khim. 2h (Russian Ed). 44(10), 1057–9,1978;
J. Chem, Soc., C(22), 2332–2,1967;
U.S. Pat. No 6271422;
Ind. Eng. Chem., Prod. Res. Develop, II(I), 88–91, 1972;
U.S. Pat. No. 3997072.

Surprisingly, the inventors have now found that a particular group of novel low fluorine content compounds with good surfactant properties may be used to prepare novel pharmaceutical aerosol formulations, and may be advantageous in terms of improving the stability of the aerosol formulation by reducing drug deposition, increasing reproducibility of the dose delivered and the like. In addition the compounds of the invention are adequately soluble in the fluorocarbon or hydrogen-containing chlorofluorocarbon propellants or mixtures thereof, obviating the need to use a polar adjuvant, such as ethanol.

Thus, in one aspect the invention provides a pharmaceutical aerosol formulation comprising a particulate medicament, one or more fluorocarbon or hydrogen-containing chlorofluorocarbon propellants and a compound of the general formula (I)

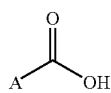

(I)

or a salt or solvate thereof, wherein:
A represents a straight chain $C_{1-16}$ alkylene substituted by n groups of formula B;
n represents an integer 1 to 3; and B independently represents $C_{1-4}$ fluoroalkyl$C_{0-6}$ alkylene-, $C_{1-4}$ fluoroalkyl$C_{0-6}$ alkylene-O—, or $C_{1-4}$ alkyl$C_{0-6}$ alkylene-O—;

wherein at least one substituent of formula B contains at least one fluorine atom and each $C_{1-4}$ fluoroalkyl moiety contains one or more fluorine atoms but not more than 3 consecutive perfluorinated carbon atoms.

In one embodiment, preferably A will represent $C_{1-12}$ alkylene, particularly $C_{3-12}$ alkylene, especially $C_{6-10}$ alkylene, most especially $C_9$ or $C_{10}$ alkylene substituted by n groups of formula B.

The n B groups may be located at any point along the straight chain $C_{1-16}$ alkylene section. It will be understood that where the B group is not located on the terminal $CH_2$—then this carbon will bear three hydrogens. Preferably a B group will be located on the terminal carbon of the $C_{1-16}$ alkylene section. Preferably the B group that is located on the terminal carbon is selected from $C_{1-4}$ fluoroalkyl$C_{0-6}$ alkylene- and $C_{1-4}$ fluoroalkyl$C_{0-6}$ alkylene-O—. The $C_{1-4}$ fluoroalkyl and $C_{1-4}$ alkyl moieties within B may be branched or straight chain. The $C_{0-6}$ alkylene moiety within B may be branched or straight chain, although preferably it will be a straight chain.

Preferably each $C_{1-4}$ fluoroalkyl- moiety contains at least two fluorine atoms, especially 3 to 5 fluorine atoms.

More preferably $C_{1-4}$ fluoroalkyl$C_{0-6}$ alkylene- of group B represents $CF_2HC_{0-9}$ alkylene-, $CF_3C_{0-9}$ alkylene-, $CF_3CF_2C_{0-8}$ alkylene, $(CF_3)_2CHC_{0-7}$ alkylene- or $(CF_3)_3CC_{0-6}$ especially $CF_3$— or $CF_3CF_2$—.

Also more preferably $C_{1-4}$ fluoroalkyl$C_{0-6}$ alkylene-O— of group B represents $CF_3C_{0-9}$ alkylene-O—, $CF_3CF_2C_{0-8}$ alkylene-O—, $(CF_3)_3CC_{0-6}$ alkylene-O—, $CF_2HC_{0-9}$ alkylene-O— or $(CF_3)_2CHC_{0-7}$ alkylene-O—.

Preferably the $C_{0-6}$ alkylene moiety of $C_{0-4}$ fluoroalkyl$C_{0-6}$ alkylene-, $C_{1-4}$ fluoroalkyl$C_{0-6}$ alkylene-O— or $C_{1-4}$ alkyl$C_{0-6}$ alkylene-O— in group B represents $C_{0-2}$ alkylene, especially $C_{0-1}$ alkylene.

More preferably, B represents $C_{1-4}$ fluoroalkyl$C_{0-6}$ alkylene-, particularly $C_{1-4}$ fluoroalkyl$C_{0-2}$ alkylene, more particularly $C_{1-4}$ fluoroalkyl$C_{0-1}$ alkylene, especially $C_{1-4}$ fluoroalkyl.

The invention includes branched compounds of formula (I) wherein n represents 2 or 3.

Preferably n represents 1 or 2, especially 1.

In particular there is provided a pharmaceutical aerosol formulation comprising a compound of the general formula (Ia)

(Ia)

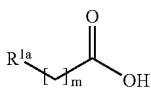

or a salt or solvate thereof, wherein:

m represents an integer 1 to 16; and $R^{1a}$ represents $C_{1-4}$ fluoroalkyl$C_{0-6}$ alkylene- or $C_{1-4}$ fluoroalkyl$C_{0-6}$ alkylene-O— wherein each $C_{1-4}$ fluoroalkyl moiety contains one or more fluorine atoms but not more than 3 consecutive perfluorinated carbon atoms.

In one aspect of the invention preferably $R^{1a}$ represents $C_{1-4}$ fluoroalkyl$C_{0-6}$ alkylene, especially $C_{1-4}$ fluoroalkyl, for example, containing at least 3 fluorine atoms e.g. 3 to 5 fluorine atoms, particularly $CF_3$— or $CF_3CF_2$—.

Preferably in this aspect m represents an integer in the range 3 to 12, especially 6 to 10 or 8 to 12, particularly 9 or 10.

More particularly the invention extends to a pharmaceutical aerosol formulation comprising a compound of the formula (Ib)

(Ib)

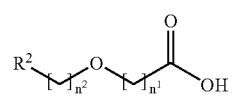

or a salt or solvate thereof, wherein:
$n^1$ represents an integer 1 to 9;

$n^2$ represents an integer 1 to 8; and $R^2$ represents $C_{1-2}$ fluoroalkyl wherein said moiety contains one or more fluorine atoms.

Preferably $R^2$ contains 3 to 5 fluorine atoms, and especially represents $CF_3$ or $CF_3CF_2$.

Preferably $n^1$ represents an integer in the range 1 to 6, especially 1 to 5 particularly 1.

Preferably $n^2$ represents an integer in the range 1 to 6, especially 3 to 6, particularly 3 or 6.

There is also provided use of compounds of formula (I) as a suspending agent in a pharmaceutical aerosol suspension formulation adapted for use in a metered dose inhaler.

Certain compounds of formula (I) are new. Therefore we provide as a further aspect of the invention a compound of formula (I) or a salt or solvate thereof with the proviso that it is not 12,12,13,13,13-pentafluorotridecanoic acid ($CF_3CF_2(CH_2)_{10}COOH$) or 12,12,12-trifluorododecanoic acid ($CF_3(CH_2)_{10}COOH$).

Preferably in the compounds of formula (I) the $C_{1-4}$ fluoroalkyl moiety contains 3 to 5 fluorine atoms, especially wherein the fluorine atoms are located on adjacent carbon atoms, particularly $CF_3$— or $CF_3CF_2$—.

Preferably for these compounds n represents 1.

Preferably B is located on the terminal carbon of the $C_{1-16}$ alkylene section of the moiety A.

A preferable series of novel compounds according to the invention are provided of the general formula (Ia')

(Ia')

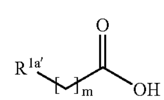

or a salt or solvate thereof, wherein:

m represents an integer 1 to 16; and $R^{1a'}$ represents $C_{1-4}$ fluoroalkyl$C_{0-6}$ alkylene- or $C_{1-4}$ fluoroalkyl$C_{0-6}$ alkylene-O— wherein each $C_{1-4}$ fluoroalkyl moiety contains at least 3 fluorine atoms but not more than 3 consecutive perfluorinated carbon atoms with the proviso that:

(i) when $R^{1a'}$ represents $C_{1-4}$ fluoroalkyl$C_{0-6}$ alkylene the compound of formula (Ia') represents something other than:

$CF_3CF_2(CH_2)_{10}COOH$;

$CF_3(CH_2)_qCOOH$;

$F_2CHCF_2CF_2CH_2COOH$;

$CF_3CHFCF_2(CH_2)_rCOOH$;

$CF_3CH(CH_3)CH_2COOH$ $CF_3CH(CH_3)(CH_2)_3COOH$;

$CF_3CH(CH_2CH_2)CH_2COOH$; or
$CF_3CH_2CH(CH_3)CH_2COOH$
wherein q represents an integer 10 or 16; and r represents 3 to 5 or 11

(ii) when $R^{1a'}$ represents $C_{1-4}$ fluoroalkyC$_{0-6}$ alkylene-O— the compound of formula (Ia') represents something other than:
$CF_3CH_2O(CH_2)_yCOOH$;
$CF_3(CH_2)_2O(CH_2)_2COOH$
$F_2CH(CF_2)_3CH_2O(CH_2)_2COOH$;
$F_2CH(CF_2)_3CH_2OCH_2COOH$;
$CF_3CH(CH_3)O(CH_2)_2COOH$
$(CF_3)_2CHOCH_2COOH$;
$CF_3CH_2CH_2OCH_2COOH$;
$CF_3OCH_2COOH$;
$F_2CHCF_2CH_2OCH_2COOH$; or
$CF_3C(F)HCF_2CH_2OCH_2CH_2COOH$
wherein y represents an integer 1, 10 or 15.

Preferably m represents an integer 3 to 12, especially 6 to 10, particularly 9 or 10.

Equally preferable is wherein m represents $C_{7-9}$ alkylene or $C_{11-15}$ alkylene, more preferably $C_8$, $C_9$, $C_{11}$ or $C_{12}$ alkylene, especially $C_9$ or $C_{11}$ alkylene.

Preferably $R^{1a'}$ represents $C_{1-4}$ fluoroalkyl- or $C_{1-4}$ fluoroalkyl-O—.

More preferably $R^{1a'}$ represents $CF_2H$—$C_{0-2}$ alkylene-$CF_3C_{0-2}$ alkylene-, $CF_3CF_2C_{0-2}$ alkylene-, $(CF_3)_2CHC_{0-1}$ alkylene-, $(CF_3)_3C$—, $CF_2HC_{0-2}$ alkylene-O—, $(CF_3)_3C$—O—, $(CF_3)_2CHC_{0-1}$ alkylene-O—, $CF_3C_{0-2}$ alkylene-O— or $CF_3CF_2C_{0-2}$ alkylene-O—, Especially preferred groups for $R^{1a'}$ are selected from $CF_2H$, $CF_3$, $CF_3CF_2$, $CF_3CF_2CH_2$, $(CF_3)_2CH$ and $(CF_3)_3C$, particularly $CF_3$ and $CF_3CF_2$.

In a first preferred subset of the series of compounds of formula (Ia') are provided the compounds of the general formula (Iaa)

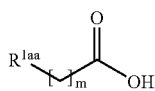

(Iaa)

or a salt or solvate thereof, wherein:
m represents an integer 1 to 16; and
$R^{1aa}$ represents $CF_3$ or $CF_3CF_2$.

In this first series preferably m represents an integer in the range 7 to 9 or 11 to 15, especially 8, 9, 11 or 12, particularly 9 or 11.

In a second preferred subset of the series of compounds of the formula (Ia') are provided compounds of the formula (Ib')

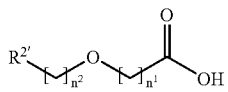

(Ib')

or a salt or solvate thereof, wherein:
$n^1$ represents an integer 1 to 9;
$n^2$ represents an integer 1 to 8; and
$R^{2'}$ represents $C_{1-2}$ fluoroalkyl wherein said moiety contains one or more fluorine atoms.

Preferably $n^1$ represents an integer 1 to 6, especially 1 to 5, particularly 1.

Preferably $n^2$ represents 1 to 6, particularly 3 to 6, especially 3, more especially 6.

Preferably $R^{2'}$ represents —$CF_3$ or —$CF_2CF_3$, more preferably —$CF_2CF_3$.

Generally when $R^{2'}$ represents $CF_3$, in compounds of formula (Ib'), compounds of particular interest are those wherein $n^1$ represents an integer in the range 3 to 9 and $n^2$ represents an integer in the range 3 to 8.

Generally when $R^{2'}$ represents $CF_3CF_2$, in compounds of formula (Ib'), compounds of particular interest are those wherein $n^1$ represents an integer in the range 1 to 9 and $n^2$ represents an integer in the range 1 to 8.

Suitable salts include alkali metal salts such as sodium and potassium and tertiary alkyl ammonium salts such as tert-butyl ammonium.

Preferably compounds of formula (I), (I'), (Ia), (Ia'), (Iaa) (Ib) and (Ib') will be present as the free acid.

Compounds of formula (I) may contain one or more chiral centres. It will be understood that compounds of formula (I) include all optical isomers of the compounds of formula (I) and mixtures thereof, including racemic mixtures thereof.

The compounds of formula (I) employed for the preparation of formulations according to the present invention are effective stabilisers of aerosol suspension formulations at low concentrations relative to the amount of medicament. Thus, the amount of compound of formula (I) employed is desirably in the range of 0.05% to 20% wtw, particularly 0.5% to 10% w/w, more particularly 0.5% to 5% w/w, relative to the medicament.

The particle size of the particulate (e.g. micronised) medicament should be such as to permit inhalation of substantially all of the medicament into the lungs or nasal cavity upon administration of the aerosol formulation and will thus be less than 100 microns, desirably less than 20 microns, and preferably will have a mass median aerodynamic diameter (MMAD) in the range 1–10 microns, e.g. 1–5 microns.

The final aerosol formulation desirably contains 0.005–10% w/w, preferably 0.005–5% w/w, especially 0.01–1.0% w/w, of medicament relative to the total weight of the formulation.

Medicaments which may be administered in aerosol formulations according to the invention include any drug useful in inhalation therapy and which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate (e.g. as sodium salt), ketotifen or nedocromil (e.g. as sodium salt); anti-infectives e.g. cephalosporins, penicillins, streptomycin, sulphonamides, tetracyclines and pentamidine; antihistamines, e.g., methapyrilene; anti-inflammatories, e.g. beclomethasone (e.g. as dipropionate), fluticasone (e.g. as propionate), flunisolide, budesonide, rofleponide, mometasone furoate, ciclesonide, triamcinolone acetonide or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; anti-tussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol, 4-hydroxy-7-[2-[[2-[[3-(2-phenylethoxy)propyl]sulfonyl]ethyl]amino]ethyl-2(3H)-benzothia-zolone; diuretics, e.g., amiloride; anticholinergics, e.g. ipratropium (e.g. as bromide), tiotropium, atropine or oxitropium; hormones, e.g. cortisone, hydrocortisone or prednisolone; xanthines, e.g. aminophylline, choline theophyllinate, lysine theophyllinate or theophylline; therapeutic proteins and peptides, e.g. insulin or glucagon. It will be clear to a person skilled in the art that, where appropriate, the medicaments may be used in the form of salts, (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant. It will be further clear to a person skilled in the art that where appropriate the medicaments may be used in the form of a pure isomer, for example, R-albuterol, R-salmeterol or RR-formoterol.

Particularly preferred medicaments for administration using aerosol formulations in accordance with the invention include anti-allergics, bronchodilators and anti-inflammatory steroids of use in the treatment of respiratory disorders such as asthma, COPD or rhinitis by inhalation therapy, for example cromoglycate (e.g. as sodium salt), albuterol (e.g. as free base or the sulphate), salmeterol (e.g. as xinafoate), formoterol (e.g. as fumarate), terbutaline (e.g. as sulphate), reproterol (e.g. as hydrochloride), a beclomethasone ester (e.g. as diproprionate), a fluticasone ester (e.g. as propionate). Salmeterol, especially salmeterol xinafoate, albuterol sulphate, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Thus suitable combinations include bronchodilators (e.g. albuterol or isoprenaline) in combination with an anti-inflammatory steroid (e.g. beclomethasone ester); a bronchodilator in combination with an anti-allergic (e.g. cromoglycate). Exemplary combinations also include: ephedrine and theophylline; fenoterol and ipratropium (e.g. as bromide); isoetharine and phenylephrine; ipratropium (e.g. as bromide) and salmeterol (particularly as xinafoate); albuterol (e.g. as free base or as sulphate) and beclomethasone ester (e.g. as dipropionate); budesonide and formoterol (e.g. as fumarate) which is of particular interest; and salmeterol (particularly as xinafoate) and fluticasone ester (e.g. as propionate) also of particular interest.

The propellants for use in the invention may be any fluorocarbon or hydrogen-containing chlorofluorocarbon or mixtures thereof having a sufficient vapour pressure to render them effective as propellants. Preferably the propellant will be a non-solvent for the medicament. Suitable propellants include, for example, $C_{1-4}$hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds, preferably binary mixtures, with other fluorocarbons or hydrogen-containing chlorofluorocarbons, for example, $CHClF_2$, $CH_2F_2$ and $CF_3CH_3$. Particularly preferred as propellants are $C_{1-4}$ hydrogen-containing fluorocarbons such as 1,1,1,2-tetrafluoroethane ($CF_3CH_2F$) and 1,1,1,2,3,3,3-heptafluoro-n-propane ($CF_3CHFCF_3$) or mixtures thereof. Preferably a single fluorocarbon or hydrogen-containing chlorofluorocarbon is employed as the propellant e.g. 1,1,1,2-tetrafluoroethane (HFA 134a) or 1,1,1,2,3,3,3-heptafluoro-n-propane (HFA 227), especially 1,1,1,2-tetrafluoroethane.

It is desirable that the formulations of the invention contain no components covered by the Montreal Protocol which provoke the degradation of stratospheric ozone. In particular, it is desirable that the formulations are substantially free of chlorofluorocarbons such as $CCl_3F$, $CCl_2F_2$ and $CF_3CCl_3$.

If desired, the propellant may additionally contain a volatile adjuvant such as a saturated hydrocarbon for example propane, n-butane, isobutane, pentane and isopentane or a dialkyl ether, for example, dimethyl ether. In general, up to 50% w/w of the propellant may comprise a volatile hydrocarbon, for example 1 to 30% w/w. However, formulations which are substantially free of volatile adjuvants are preferred. In certain cases, it may be desirable to include appropriate amounts of water, which can be advantageous in modifying the dielectric properties of the propellant.

Polar adjuvants which may, if desired, be incorporated into the formulations according to the present invention include e.g. $C_{2-6}$aliphatic alcohols and polyols such as ethanol, isopropanol and propylene glycol and mixtures thereof. Preferably ethanol will be employed. In general only small quantities (e.g. 0.05 to 3.0% w/w) of polar adjuvants are required and the use of quantities in excess of 5% w/w may disadvantageously tend to dissolve the medicament. Formulations preferably contain less than 1% w/w, e.g. about 0.1% w/w of polar adjuvant. Polarity may be determined, for example, by the method described in European Patent Application Publication No. 0327777.

However, as the compounds of formula (I) are adequately soluble in the fluorocarbon or hydrogen-containing chlorofluorocarbon propellant the need to use a polar adjuvant is obviated. This is advantageous as polar adjuvants especially ethanol are not suitable for use with all patient groups. Formulations containing a compound of formula (I) which avoid use of a polar adjuvant are preferred.

In addition to one or more compounds of the general formula (I), the formulations according to the present invention may optionally contain one or more further ingredients conventionally used in the art of pharmaceutical aerosol formulation. Such optional ingredients include, but are not limited to, taste masking agents, sugars, buffers, antioxidants, water and chemical stabilisers.

A particularly preferred embodiment of the invention provides a pharmaceutical aerosol formulation consisting essentially of one or more particulate medicament(s), one or more fluorocarbon or hydrogen-containing chlorofluorocarbon propellant(s) and one or more compound(s) of formula (I), (Ia) or (Ib).

A further embodiment of the invention is a sealed container capable of withstanding the pressure required to maintain the propellant as a liquid, such as a metered dose inhaler, containing therein the aerosol formulation as described above.

The term "metered dose inhaler" or MDI means a unit comprising a can, a secured cap covering the can and a formulation metering valve situated in the cap. MDI system includes a suitable channeling device. Suitable channeling devices comprise, for example, a valve actuator and a cylindrical or cone-like passage through which medicament may be delivered from the filled canister via the metering valve to the nose or mouth of a patient such as a mouthpiece actuator.

As an aspect of this invention there is also provided a process for the preparation of compounds of formula (I) which comprises:

(A1) reacting a halogenated derivative with a reducing agent, e.g. in the preparation a compound of formula (Ia) wherein $R^{1a}$ represents $C_{1-4}$ fluoroalkyl$C_{0-6}$ alkylene- and m represents an integer 2 to 16 by reacting a compound of formula (IIa)

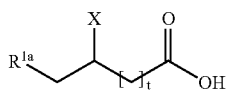
(IIa)

or a salt or a solvate thereof or a derivative thereof wherein the carboxylic acid group is protected and wherein $R^{1a}$ represents $C_{1-4}$ fluoroalkyl$C_{0-6}$ alkylene-, X represents a halogen and t is an integer in the range 0 to 14, with a reducing agent followed, if necessary, by deprotection of the carboxylic acid; or (A2) reducing a corresponding compound containing a C=C double bond e.g. in the preparation of a compound of formula (Ia) wherein $R^{1a}$ represents $C_{1-4}$ fluoroalkyl$C_{0-6}$ alkylene- and m represents an integer 2 to 16 by reacting a compound of formula (IIIa)

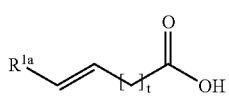
(IIIa)

or a salt or a solvate thereof or a derivative thereof wherein the carboxylic acid group is protected and wherein $R^{1a}$ is as just defined and t is an integer in the range 0 to 14, with a reducing agent followed, if necessary, by deprotection of the carboxylic acid or in the preparation of a compound of formula (Ia) whebrein $R^{1a}$ represents $C_{1-4}$ fluoroalkyl$C_{0-6}$ alkylene- and m represents an integer 3 to 16 by reacting a compound of formula (IVa)

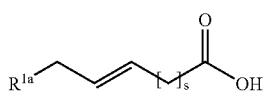
(IVa)

or a salt or a solvate thereof or a derivative thereof wherein the carboxylic acid group is protected and wherein $R^{1a}$ is as defined in process (A1) and s is an integer in the range 0 to 13 with a reducing agent followed, if necessary, by deprotection of the carboxylic acid; or (A3) ox(idising a corresponding alcohol to the carboxylic acid e.g. in the preparation of compounds of formula (Ia) oxidising a compound of formula (Va)

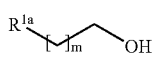
(Va)

wherein, $R^{1a}$ and m are as defined above for compounds of formula (Ia), to the corresponding carboxylic acid; or (A4) converting a corresponding compound of formula (I) wherein the carboxylic acid is masked to a free carboxylic adid e.g. in the preparation of compounds of formula (Ia) by converting a compound of formula (VIa)

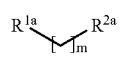
(VIa)

wherein $R^{1a}$ and m are as defined above for compounds of formula (Ia) and $R^{2a}$ represents a moiety which is a masked acid such as cyano, acetal or —C=CH$_2$, into the corresponding carboxylic acid by, for example, hydrolysis, hydrolysis and oxidation or oxidative cleavage; or (A5) creating a carbon-carbon bond to form a compound of formula (I) by means of an organo-metallo reagent e.g. in the preparation of a compound of formula (Ia) wherein $R^{1a}$ and m are as defined above for compounds of formula (Ia) by reacting a compound of formula (VIIa)

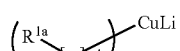
(VIIa)

wherein $R^{1a}$ is defined above and $m^1$ represents an integer in the range 0 to 16 and Cu represents copper and Li represents lithium, with a compound of formula (VIIIa)

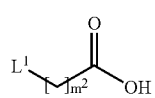
(VIIIa)

or a salt or a solvate thereof or a derivative thereof wherein the carboxylic acid is protected, wherein $m^2$ represents an integer 1 to 16 and $L^1$ represents a leaving group, followed, if necessary, by deprotection of the carboxylic acid with the proviso that $m^1+m^2$ represents an integer in the range 1 to 16, or in the preparation of a compound of formula (Ia) wherein $R^{1a}$ and m are as defined above for compounds of formula (Ia), by reacting a compound of formula (IXa)

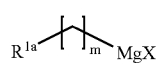
(IXa)

wherein $R^{1a}$ and m are as defined above for compounds of formula (Ia), Mg represents magnesium and X represents a halogen, with carbon dioxide;

(A6) preparing a compound of formula (I) in which B represents a group of formula $C_{1-4}$ fluoroalkyl-$C_{0-6}$ alkylene-O— by reacting a compound of formula (Xa)

$C_{1-4}$ fluoroalkyl$C_{0-6}$ alkylene-OH  (Xa)

with a compound containing a leaving group e.g. in the preparation of a compound of formula (Ia) wherein $R^{1a}$ represents $C_{1-4}$ fluoroalkyl$C_{0-6}$ alkylene-O— and m represents an integer 1 to 16 by reacting an alcohol of formula (Xa) or the corresponding anion thereof with a compound of formula (VIIIa) or a salt or a solvate thereof or a derivative thereof wherein the carboxylic acid is protected; or (A7) preparing a compound of formula (I) in which B represents a group of formula $C_{1-4}$ fluoroalkyl-$C_{0-6}$ alkylene-O— by reacting a compound of formula (Xb)

$$C_{1-4} \text{ fluoroalkyl} C_{0-6} \text{ alkylene-}L^2 \quad (Xb)$$

wherein $L^2$ represents a leaving group with an alcohol e.g. in the preparation of a compound of formula (Ia) wherein $R^{1a}$ represents $C_{1-4}$ fluoroalkyl$C_{0-6}$ alkylene-O— and m represents an integer 1 to 16, by reacting a compound of formula (Xb) with a compound of formula (XIa)

(XIa)

or a salt or a solvate thereof or a derivative thereof wherein the carboxylic acid is protected and wherein m is as defined above for compounds of formula (Ia); or (A8) preparing a compound of formula (I) in which B represents a group of formula $C_{1-4}$ fluoroalkyl-$C_{0-6}$ alkylene-O— by reacting a compound of formula (Xa) as defined above with a compound of formula (VIIIa) as defined above;

(A9) deprotecting a protected compound of formula (I).

In process (A1) the carboxylic acid is preferably protected e.g. as an ester such as a $C_{1-4}$alkyl ester or a benzyl ester. Examples of protecting groups (e.g. for carboxylic acids) and means for their removal can be found in "Protecting Groups In Organic Synthesis" by Theodora Green and Peter G. M Wuts (John Wiley and Sons Inc 1999). Suitable carboxylic acid protecting groups include but are not limited to carboxylic acid esters e.g. ethyl ester, aryl esters e.g. benzyl ester.

Protecting groups can be removed by acid or base catalysed hydrolysis or reduction, for example, catalytic hydrogenation. Where the carboxylic acid is protected as the benzyl ester, the protecting group may be removed, for example, by catalytic hydrogenation. Where the carboxylic acid is protected as the $C_{1-4}$alkyl ester, the protecting group may be removed, for example, by base hydrolysis.

In process (A1) the term "reducing agent" is a term well understood by persons skilled in the art and can include hydride sources like borohydrides and alkali metal borohydrides, but would also include hydrogen in catalytic hydrogenation wherein a suitable catalyst such as palladium on carbon may be used.

Other suitable hydride sources include sodium triacetoxyborohydride, tetrabutylammonium triacetoxyborohydride, sodium cyanoborohydride, polymer bound borohydride or sodium borohydride in a solvent such as acetic acid wherein triacetoxyborohydride is formed in situ, diborane or a complex metal hydride. Generally the reaction would be performed in an inert solvent, for example, tetrahydrofuran (THF) or dichloromethane (DCM) under non-extreme conditions e.g. −10 to 50° C. such as 0° C. in an inert atmosphere such as nitrogen. When X represents iodine, Zn may be employed as the reducing agent as described in J Fluorine Chem (1999) 93, 107–115 (Graupe et al) or alternatively in J Org. Chem. (1962) 27, 4491–4498 (Brace et al). However when the latter method is used, catalytic hydrogenation may still be required to ensure complete conversion to a compound of formula (I) because compounds of formula (IIIa) and/or (IVa) may be present.

Catalytic hydrogenation is preferred for process (A1).

Catalytic hydrogenation conditions analogous to those described above for use in process (A1) are suitable for use in process (A2).

In process (A3) methods for oxidising a primary alcohol to the corresponding carboxylic acid, using strong oxidising agents are well known to persons skilled in the art. Suitable reagents include: chromic acid, chromic (VI) oxide, permanganate e.g. potassium permanganate, and nitric acid. Permanganate is preferred for use in process (A2), especially potassium permanganate.

The oxidation will usually be performed in an inert solvent e.g. THF, water or using one of the reagents as a solvent under non-extreme conditions e.g. 0 to 100° C. such as 75° C. in an inert atmosphere such as nitrogen.

In process (A4) a, masked carboxylic acid group is a moiety which can readily be converted to a free carboxylic acid usually at a late stage in the synthesis once other functionality has been introduced into the molecule.

The hydrolysis of a cyano group to form the corresponding free carboxylic acid may be performed using an aqueous acid e.g. aqueous hydrochloric, nitric or sulphuric acid wherein the acid acts as the solvent. Mixtures of acids such as aqueous hydrochloric and acetic acid wherein the acetic acid is the solvent may be used. The reactions of this type may be performed under non-extreme conditions e.g. −10 to 50° C. such as room temperature. Wherein the carboxylic acid is masked as an acetal, hydrolysis under normal condition may be concomitant with or followed by oxidation by conventional methods.

Alternatively wherein the carboxylic acid group is masked as a double bond, it may be converted to the free carboxylic acid by oxidative cleavage with, for example, and acid permanganate or acid dichromate such potassium permanganate or chromium trioxide, in a solvent such as water under non-extreme conditions. The potassium permanganate may be used in conjunction with a reagent such as $HIO_4$ or $NaIO_4$ (Advanced Organic Chemistry Reactions Mechanisms and Structures fourth edition, Jerry March page 1181). In these reactions the carbon chain length of the free carboxylic acid is at least one carbon shorter than the chain length of the compound containing the uncleaved double bond. Therefore it is important to take this into consideration when choosing the relevant starting materials.

Processes using organo-metallo reagents, as in process (A5), are usually performed in an inert substantially anhydrous solvent e.g. THF in an inert atmosphere such as nitrogen at a non-extreme temperature e.g. −10 to 50° C. such as 0° C. Preferably the carboxylic acid group will be protected during the reaction, for example, as a carboxylic acid ester.

Suitable leaving groups for $L^1$ include, for example, halogens such as chloro, bromo and iodo, —Otriflyl, —Otosyl and —Omesyl.

Process (A6) will usually be performed in an inert solvent e.g. THF or DMF in the presence of base such as a non-nucleophilic or sterically hindered base e.g. Hunig's base or hydride (employing the alkoxide as reagent) at non-extreme temperatures e.g. −10 to 50° C. such as room temperature. Where the reagent is, for example, an alkoxide such as sodium alkoxide the corresponding alcohol may be used as the solvent. It will be clear to a skilled person that this reaction may be performed wherein the double bond is located at any point along the alkylene chain.

Preferably the carboxylic acid moiety in compounds of formula (VIIIa) will be protected in processes (A5) or (A6). Suitable protecting groups include those described above for process (A1).

Process (A7) will be performed under conditions suitable for nucleophilic substitution which will be well known to a person skilled in the art.

Process (A8) may be performed under conditions analogous to those described above for process (A6).

Examples of protecting groups and means for their removal according to process (A9) are discussed above in process (A1).

Suitable leaving groups for $L^2$ include those described above for $L^1$.

A process for the preparation of a compounds of formula (IIa) wherein $R^{1a}$ represents $C_{1-4}$ fluoroalkyC$_{1-6}$ alkylene- and t represents an integer 0 to 14, comprises reacting a compound of formula (XIIa)

  (XIIa)

wherein $R^{1a}$ represents $C_{1-4}$ fluoroalkyleneC$_{0-6}$ alkylene- and X is a halogen with a compound of formula (XIIIa)

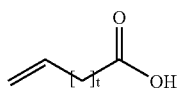  (XIIIa)

or a salt or a solvate thereof or a derivative thereof wherein the carboxylic acid is protected and t represents an integer in the range 0 to 14.

The process described above for the preparation of compounds of formula (IIa) may be performed under free radical conditions e.g. in the presence of a peroxide (such as benzyl peroxide) or 2,2-Azobis(isobutyronitrile) (AIBN) at a non-extreme temperature such as 0 to 100° C. such as 70° C. The alkylene reagent acts as the solvent. Further details of suitable reaction conditions may be obtained by reference to J Org. Chem. (1962) 27, 4491–4498 (Brace et al) which illustrates use of trifluoroiodomethane as a compound of formula (XIIa). Compounds of formula (IIa) in which X represents halogen may also be prepared from corresponding compounds of formula (IIIa), e.g. by treatment with a hydrohalic acid.

Compounds of formula (IIIa) may be prepared by eliminating the halogen X from compounds of formula (IIa), for example, using the zinc acetic acid method described above for process (A1) or using KOH in an alcohol solvent. Alternatively the double bond may be formed using the Wittig reaction or the dehydration of an alcohol to give the required double bond, using methodology well known to a person skilled in the art.

An alcohol may be dehydrated, for example, by using a concentrated acid.

Analogous methodology may be used to prepare compounds of formula (IVa).

The alcohol moiety in compounds of formula (Va) may be prepared from an alkene, for example, by hydroboration such as in the presence of diborane and subsequent treatment with hydrogen peroxide and hydroxide.

Alternatively compounds of formula (Va) can be prepared by methodology analogous to that described above by reducing a compound analogous to compounds of formula (IIa), (IIIa) or (IVa) but wherein the said molecule contains a protected or masked alcohol rather than a carboxylic acid moiety.

A masked alcohol is a group that can readily be converted into an alcohol at a later stage in the synthesis, for example an ether.

Compounds of formula (VIa) wherein the carboxylic acid is masked as a cyano group may be prepared by reacting a compound of formula (XIVa)

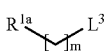  (XIVa)

wherein $R^{1a}$ is as defined above, m represents 1 to 16 and $L^3$ represents a leaving group, with a cyanide nucleophile as generated from, for example, sodium cyanide.

Suitable conditions for such a reaction are well known to persons skilled in the art. Where the carboxylic acid is masked as an alkene the double bond may be prepared by, for example, dehydration of a compound of formula (Va) as defined above. Acetals can be prepared by reacting a corresponding aldehyde with an alcohol in the presence of an acid catalyst.

Other compounds of formula (VIa) may be prepared by known methods.

Compounds of formula (VIIa) may be prepared by reacting two molar equivalents of a compound of formula (IXb)

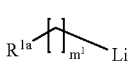  (IXb)

wherein $R^{1a}$ is as defined above, $m^1$ represents an integer in the range 0 to 16 and Li represents lithium metal, with a cuprous halide in an inert substantially anhydrous solvent such as ether at non-extreme temperatures e.g. −10 to 30° C., such as 0° C.

Compounds of formula (VIIIa) may be prepared from a corresponding compound of formula (XIa) by converting the alcohol into a good leaving group by, for example, reacting it with a halogenating agent such hydrobromic acid or thionyl chloride or para-tolunesulphonic acid under conditions well known to persons skilled in the art. It may be necessary to protect the carboxylic acid during the reaction to convert the alcohol into a good leaving group.

Compounds of formula (IXa) may be prepared by reacting compounds of formula (XIVa) in which $L^3$ represents chloro, bromo or iodo with magnesium metal in an inert substantially anhydrous solvent such as THF at non-extreme temperatures such as −10 to 30° C., such as 0° C.

Compounds of formula (IXb) can be prepared from compounds of formula (XIVa) using lithium metal by analogous methodology to that described above for the preparation of compounds of formula (IXa).

Compounds of formula (XIIIa) may be prepared by dehydrating an alcohol to form the terminal double bond or alternatively use of the Wittig reaction under conditions well known to persons skilled in the art.

Compounds of formula (XIVa) may be prepared from compounds of formula (Va) by converting the alcohol into a good leaving group by, for example, reacting it with a halogenating agent such hydrobromic acid or thionyl chloride or para-tolunesulphonic acid under conditions well known to persons skilled in the art.

Compounds of formula (Xa), (Xb), (XIa) and (XIIa) are known or can be prepared by known methods.

Other compounds of formula (I) and intermediates thereto may be prepared by analogous processes to those described above or by conventional processes known per se.

Certain intermediate compounds are new and form an aspect of the invention.

In addition, processes for preparing formulations including one or more compounds of formula (I) form an aspect of this invention.

The formulations of the invention may be prepared by dispersal of the medicament and a compound of formula (I) in the selected propellant in an appropriate container, e.g. with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The suspension stability of the aerosol formulations according to the invention may be measured by conventional techniques, for example by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204–207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber expressed as a percentage of the total amount of active ingredient delivered per actuation using the twin impinger method described above.

MDI canisters generally comprise a container capable of withstanding the vapour pressure of the propellant used such as a plastic or plastic-coated glass bottle or preferably a metal can, for example aluminium or an alloy thereof which may optionally be anodised, lacquer-coated and/or plastic-coated (e.g. incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g., see Byron, above and WO/96/32099). Preferably the canister is fitted with a cap assembly, wherein a drug metering valve is situated in the cap, and said cap is crimped in place.

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, black and white butadiene-acrylonitride rubbers, EPDM rubber, butyl rubber and neoprene. Suitable valves are commercially available from manufacturers well known in the aerosol industry, for example, from Valois, France (eg. DF10, DF30, DF60), Bespak plc. UK (e.g. BK300, BK357) and 3M-Neotechnic Ltd, UK (e.g. SPRAYMISER™).

A further aspect of this invention comprises a process for filling the said formulation into MDIs.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquefied propellant is pressure filled through the charge vessel into a manufacturing vessel, together with liquefied propellant containing the surfactant. The drug suspension is mixed before recirculation to a filling machine and an aliquot of the drug suspension is then filled through the metering valve into the canister.

In an alternative process, an aliquot of the liquefied formulation is added to an open canister under conditions which are sufficiently cold to ensure formulation does not vaporise, and then a metering valve crimped onto the canister.

Typically, in batches prepared for pharmaceutical use, each filled canister is check-weighed, coded with a batch number and packed into a tray for storage before release testing.

Each filled canister is conveniently fitted into a suitable channeling device prior to use to form a metered dose inhaler system for administration of the medicament into the lungs or nasal cavity of a patient. Metered dose inhalers are designed to deliver a fixed unit dosage of medicament per actuation or "puff", for example in the range of 10 to 5000 micrograms of medicament per puff.

Administration of medicament may be indicated for the treatment of mild, moderate, severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time.

Suitable daily doses, may be, for example in the range 50 to 200 micrograms of salmeterol, 100 to 1000 micrograms of albuterol, 50 to 2000 micrograms of fluticasone propionate or 100 to 2000 micrograms of beclomethasone dipropionate, depending on the severity of the disease.

Thus, for example, each valve actuation may deliver 25 micrograms of salmeterol, 100 micrograms of albuterol, 25, 50, 125 or 250 micrograms of fluticasone propionate or 50, 100, 200 or 250 micrograms of beclomethasone dipropionate. Doses for Seretide™, which is a combination of salmeterol and fluticasone propionate, will usually be those given for the corresponding individual component drugs. Typically each filled canister for use in a metered dose inhaler contains 60, 100, 120, 160 or 240 metered doses or puffs of medicament.

An appropriate dosing regime for other medicaments will be know or readily available to persons skilled in the art.

The use of the compounds of formula (I) as described above especially in the preparation of a pharmaceutical formulation; use of a formulation as described above in inhalation therapy e.g. for the treatment or prophylaxis of respiratory disorders; and use of a metered dose inhaler system in the treatment or prophylaxis of respiratory disorders are all alternative aspects of this invention.

A still further aspect of the present invention comprises a method of treating respiratory disorders such as, for example, asthma, which comprises administration by inhalation of an effective amount of a formulation as herein described.

The following non-limiting examples serve to illustrate the invention.

EXAMPLES

General Analytical Conditions

Electron impact GCMS was conducted on a $HPGC_{1800}A$ GCD with HP7673A autosampler and column HP5 5% phenyl methyl siloxane 30 m×0.25 mm×0.25 μm. The gradient: temperature ramp 60 to 300° C. at 15 deg/min. The total run time was 15 mins with a splitless injection and the carrier gas was helium at 1 ml/min.

Mass spectra were conducted on a HP5989A Engine Mass spectrometer using positive thermospray ionisation.

Example 1

11,11,12,12,12-Pentafluorododecanoic acid
a) Methyl dec-2-enoate

To a stirred solution of 9-decanoic acid (40 g) in methanol (400 ml) was added concentrated sulphuric acid, S.G 1.84 (0.5 ml) and the reaction was stirred and heated at reflux for 3 hours. The reaction mixture was allowed to cool to 20° C., poured onto water (50 ml) and then extracted with diethyl ether (3×200 ml). The ether extracts were combined, dried and the solvent was removed in vacuo to leave the title compound as a pale yellow oil (42 g).

GC/MS—202 m/z [$MNH_4^+$], retention time 7.18 mins (b) Methyl 11,11,12,12,12-pentafluoro-9-iodododecanoate Perfluoroethyl iodide (5.1 ml) was condensed using a cardice trap and quickly transferred into a high-pressure hastalloy vessel containing the product from step (a) (5 g) and benzoyl peroxide (0.12 g). The reaction vessel was heated at 70° C. for 3 hours. The reaction mixture was allowed to cool to 20° C. and the excess perfluoroethyl iodide was removed in vacuo to leave the title compound as a pale yellow oil (10.94 g).

GC/MS—448 m/z [$MNH_4^+$], retention time 8.95 mins (c) Methyl 11,11,12,12,12-pentafluorododecanoate To a stirred solution of the product from step (b) (2.5 g) in acetic acid (15 ml) was added zinc dust (0.75 g) and the reaction stirred at 20° C. for 17 hours. The reaction mixture was then filtered through a celite pad. The solvent was removed from the filtrate in vacuo to leave a dark orange residue that was partitioned between ethyl acetate (20 ml) and water (20 ml). The ethyl acetate layer was washed with saturated sodium bicarbonate solution (10 ml), dried and the solvent was removed in vacuo to leave the title compound as a dark red oil (1.66 g). A 1:6 mixture of elimination by-product:product, respectively, was produced.

GC/MS—322 m/z [$MNH_4^+$], retention time 7.49 mins (d) Methyl 11,11,12,12,12-pentafluorododecanoate To a stirred solution of the product from step (c) (1.6 g) in ethanol (16 ml) was added palladium catalyst, (10% on carbon, degussa type, 0.24 g). The reaction was stirred at 20° C. at 60 psi for 17 hours. The reaction mixture was then filtered through a celite pad and the filtrate was evaporated in vacuo to leave the title compound as a dark orange oil (1.5 g). GC/MS-322 m/z [$MNH_4^+$], retention time 7.49 mins (e) 11,11,12,12,12-Pentafluorododecanoic acid To a stirred solution of the product from step (d) 2:1 in methanol:water (25 ml:12 ml) was added sodium hydroxide pellets (0.8 g). The reaction was heated at reflux for 1 hour. After cooling the reaction mixture to 20° C. the solvent was removed in vacuo. The residue was acidified to pH1 using concentrated hydrochloric acid and then partitioned between ethyl acetate and water. The combined organic extracts were dried and the solvent was removed in vacuo to leave the title compound as a white crystalline solid (1 g).

GCMS—308 m/z [$MNH_4^+$], retention time 7.99 mins

Other compounds which may be prepared by methods analogous to those given above for Example 1:

Example 2

13,13,13-Trifluorotridecanoic acid

The preparation of this compound was analogous to the synthesis of Example 1, apart from the use of the reagents undecylenic acid in step (a) and 2-iodo-1,1,1-trifluoroethane in step (b).

GC-MS—269 m/z [$MH^+$], retention time 8.59 mins (methane adduct)

Example 3

12,12,12-Trifluorododecanoic acid

The preparation of this compound was analogous to the synthesis of Example 1, apart from the use of the reagent 2-iodo-1,1,1-trifluoroethane in step (b).

GC-MS—255 m/z [$MH^+$], retention time 8.31 mins (methane adduct)

Example 4

12,12,13,13,13-Pentafluorotridecanoic acid

The preparation of this compound was analogous to the synthesis of Example 1, apart from the use of the reagent undecylenic acid in step (a).

GC-MS—322 m/z [$MNH_4^+$], retention time 8.20 mins

Example 5

[(7,7,8,8,8-Pentafluorooctyl)oxy]acetic acid

To a stirred solution of 6-(pentafluoroethyl)hexan-1-ol (500 mg) in tetrahydrofuran (10 ml) was added sodium hydride (60% dispersion in mineral oil; 118 mg) and the reaction was stirred at 20° C. for 30 mlnutes. Ethyl bromoacetate (379 mg) was added and the reaction was stirred for a further 3 hours. The reaction was quenched by the addition of ethanol (3 ml) followed by stirring for 30 mInutes, then 2M sodium hydroxide (3 ml) was added and the reaction was stirred for a further 2 hours. The reaction mixture was partitioned between dichloromethane (100 ml) and water (100 ml). The aqueous layer was acidified to pH 1 by the addition of 2M hydrochloric acid and then extracted with dichloromethane (3×100 ml). The combined organic layers were dried over magnesium sulphate and the solvent was removed in vacuo to give the title compound as a white solid (250 mg).

Mass spectrum m/z 296 [$MNH_4^+$]

$R_f$ 0.15 (dichloromethane:methanol:880 ammonia solution 200:20:1)

Other compounds which may be prepared by methods analogous to those given above for example 5:

Example 6

(2,2,3,3,3-Pentafluoronpropoxy)acefic acid

The preparation of this compound was analogous to the synthesis of Example 5, apart from the use of the reagent 2,2,3,3,3-pentafluoro-1-propanol.

Mass spectrum m/z 226 [$MNH_4^+$]

$R_f$ 0.15 (dichloromethane:methanol:880 ammonia solution 100:15:1)

Example 7

[(4,4,5,5,5-Pentafluoronentyl)oxy]acefic acid

The preparation of this compound was analogous to the synthesis of Example 5, apart from the use of the reagent 4,4,5,5,5-pentafluoropentan-1-ol.

Mass spectrum m/z 254 [$MNH_4^+$]

$R_f$ 0.15 (dichloromethane:methanol:880 ammonia solution 100:12:1)

Example 8

6-[(4,4,5,5,5-Pentafluoropentyl)oxy]hexanoic acid a) Ethyl 6-{[(4-methylphenyl)sulfonyl]oxy}hexanoate To a stirred solution of ethyl-6-hydroxyhexanoate (2 g) and triethylamine (1.5 ml) in dichloromethane (5 ml) was added fptoluenesulphonyl chloride (2.6 g) and the reaction was stirred at 20° C. for 18 hours. The reaction mixture was diluted with dichloromethane (250 ml), washed with water (250 ml) and brine (100 ml), dried over magnesium sulphate and the solvent was removed in vacuo. Purification by column chromatography on silica gel (Biotage) eluting with 18% ethyl acetate in cyclohexane gave the title compound as a white solid (3 g).

Mass spectrum m/z 332 [$MNH_4^+$]

b) Ethyl 6-[(4,4,5,5,5-pentafluoropentyl)oxy]hexanoate

To a stirred solution of the product of step (a) (500 mg) and 4,4,5,5,5-pentafluoropentan-1-ol (284 mg) in tetrahydrofuran (10 ml) was added potassium tert-butoxide (1M in tetrahydrofuran; 1.6 ml) and the reaction was stirred at 200° C. for 2 hours. An additional charge of potassium tert-butoxide (1M in tetrahydrofuran; 1.6 ml) was added and the reaction was stirred for a further 18 hours. Ethanol (5 ml) was added and the reaction was stirred for 30 mInutes. The reaction mixture was partitioned between dichloromethane (300 ml) and water (300 ml). The organic layer was dried over magnesium sulphate and the solvent was removed in vacuo. Purification by column chromatography on silica gel (5 g Bond Elut cartridge) eluting with 20% ethyl acetate in cyclohexane gave the title compound as a clear oil (100 mg).

Mass spectrum m/z 338 [$MNH_4^+$]

c) 6-[(4,4,5,5,5-Pentafluoropentyl)oxy]hexanoic acid

To a stirred solution of the product of step (b) in 1,4-dioxane (5 ml) was added 0.1M sodium hydroxide solution (5 ml) and the reaction was stirred at 20° C. for 4 hours. The reaction volume was reduced by 50% in vacuo and then partitioned between water (50 ml) and dichloromethane (50 ml). The aqueous layer was acidified to pH 1 by the addition of 2M hydrochloric acid and then extracted with dichloromethane (3×50 ml). The combined organic layers were dried over magnesium sulphate and the solvent was removed in vacuo to give the title compound as a white solid (30 mg).

Mass spectrum m/z 310 [$MNH_4^+$]

$R_f$ 0.17 (dichloromethane:methanol:880 ammonia solution 200:20:1)

Experimental Data

Sample Preparation

Salmeterol xinafoate formulations in HFA 134a, of strength 25 μg per actuation, and 10% w/w (relative to drug) of the relevant surfactant compound of formula (I) were prepared using salmeterol xinafoate (5.8 mg), HFA 134a (12 g) and the relevant compound (0.58 mg). The control was prepared without the addition of a surfactant.

Table 1 shows mean particle size data determined by image analysis using a Galai CIS-100 particle size analyser for sample formulations prepared as described above. In this measurement, particle size is represented as the equivalent diameter of a circle of equal area to the object. The mean is the average of 4 determinations. The particle size measurement was obtained by transferring the suspensions to a presurised cell, and video-imaging the sample under shear via a microscope objective.

The equivalent diameter is defined as the diameter of a circle of equal area to the object.

$$\text{Equivalent Diameter} = \sqrt{\frac{\text{Area}}{\pi}}$$

The mean equivalent diameter can be weighted by number, length or volume. e.g. For three particles with equivalent diameters of x, y and z:

$$\text{Mean Number weighted diameter} = \left(\frac{1}{3}\right)x + \left(\frac{1}{3}\right)y + \left(\frac{1}{3}\right)z$$

Mean Length weighted diameter =

$$\left(\frac{x}{x+y+z}\right)x + \left(\frac{y}{x+y+z}\right)y + \left(\frac{z}{x+y+z}\right)z$$

The data shows that compounds of formula (I) according to the invention may have suspension stabilising properties thereby discouraging flocculation of drug particles. This is seen by the significant reduction in average particle size ("mean length weighted diameter") when a compound as described in example 5 is incorporated into the formulation. Furthermore the standard deviation and relative standard deviation which is a measure of the the spread of the data range is advantageously reduced in the formulation containing the said surfactant compound in comparision the control.

TABLE 1

Particle Size Data

| | Mean Length weighted diameter μm | Standard Deviation μm | Relative Standard Deviation |
|---|---|---|---|
| Control | 29.3 | 1.7 | 5.7 |
| Example 5 | 13.8 | 0.5 | 3.4 |

Andersen Cascade Impaction

The profile obtained using an Anderson cascade impactor may be used to analyse certain properties of pharmaceutical aerosol formulations such as the fine particle mass fraction which is a measure of the proportion of the drug likely to reach the therapeutic target in the lungs.

Content Uniformity

The content uniformity of the formulation, the preparation of which is described above, was assessed by dose through use testing. Testing was performed on 10 cans/inhalers at "beginning of use" (BoU) and "end of use" (EoU). After each inhaler had been primed (4 shots fired to waste), actuations 1 and 2 (BoU) were collected. The next 116 actuations of each inhaler were then fired to waste using an automated method and actuations 119 and 120 (EoU) collected.

The assesment of content uniformity was performed intially (following sample preparation). The results are quoted in Table 2 as the mean of the two BoU actuations for 10 inhalers (1+2 for 10 inhalers) and the mean of two EoU actuations for the said 10 inhalers (119+120 for the same 10 inhalers) together with the percentage relative standard deviation (% RSD).

The data shows that, in the presence of the surfactant compound of Example 5, there is a decrease in the difference between the dose collected at the beginning and end of use. In the control there is a rise from beginning to end of use of 5.5 μg. However, in the presence of the said surfactant compound advantageously this rise is reduced to 1.8 μg. Also there is a reduction in the percentage RSD, particularly for the EoU results, for the 10 inhalers tested which shows improved can to can reproducibility. The presence of the surfactant therefore improves the content uniformity of the inhalers tested.

TABLE 2

Content Uniformity

| Control | | Example 5 | |
|---|---|---|---|
| BoU dose μg | EoU dose μg | BoU dose μg | EoU dose μg |
| 17.3 (5.5% RSD) | 22.8 (8.1% RSD) | 19.0 (5.2% RSD) | 21.8 (5.3% RSD) |

It will be understood that the present disclosure is for the purpose of illustration only and the invention extends to modifications, variations and improvements thereto which will be within the ordinary skill of the person skilled in the art.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:

1. A pharmaceutical aerosol formulation comprising a compound of formula (Ib)

$$R^2 \diagdown_{n^2} O \diagdown_{n^1} \underset{O}{\overset{O}{\diagup}} OH \qquad (Ib)$$

or a salt or solvate thereof, wherein:
 $n^1$ represents an integer 1 to 6;
 $n^2$ represents an integer 1 to 8; and
 $R^2$ represents $C_{1-2}$ fluoroalkyl wherein said $C_{1-2}$ fluoroalkyl contains one or more fluorine atoms.

2. A pharmaceutical aerosol formulation according to claim 1 wherein $R^2$ represents $CF_3$ or $CF_3CF_2$.

3. A pharmaceutical aerosol formulation according to claim 1 wherein $n^2$ represents 1 to 6.

4. A pharmaceutical aerosol formulation according to claim 3 wherein $n^2$ represents 3 to 6.

5. A pharmaceutical aerosol formulation according to claim 3 wherein $n^2$ represents 6.

6. A pharmaceutical aerosol formulation according to claim 1 wherein $n^1$ represents 1.

7. A pharmaceutical aerosol formulation according to claim 1 wherein the compound of formula (Ib) is:
 [(7,7,8,8,8-pentafluorooctyl)oxy] acetic add;
 (2,2,3,3,3-pentafluoropropoxy) acetic acid;
 [(4,4,5,5,5-pentafluoropentyl)oxy] acetic acid;
 6-[(4,4,5,5,5-pentafluoropentyl)oxy] hexanoic add;
 or a salt or solvate of any one thereof.

8. A pharmaceutical aerosol formulation according to claim 7 wherein the compound of formula (Ib) is [(7,7,8,8,8-pentafluorooctyl)oxy] acetic acid or salt or solvate thereof.

9. A pharmaceutical aerosol formulation according to claim 1 where the compound of formula (Ib) is present as the free acid.

10. A pharmaceutical aerosol formulation according to claim 1 further comprising a fluorocarbon propellant selected from the group consisting of 1,1,1,2-tetrafluoroethane, 1,1,1,2,3,3,3-heptafluoro-n-propane, and mixtures thereof.

11. A pharmaceutical aerosol formulation according to claim 10 wherein the propellant is 1,1,1,2-tetrafluoroethane.

12. A pharmaceutical aerosol formulation according to claim 1 further comprising a particulate medicament selected from the group consisting of albuterol or a physiologically acceptable salt thereof, fluticasone propionate or a physiologically acceptable solvate thereof, and salmeterol or a physiologically acceptable salt thereof.

13. A pharmaceutical aerosol formulation according to claim 1 wherein the formulation further comprises an additional medicament.

14. A pharmaceutical aerosol formulation according to claim 13 which comprises salmeterol or a physiologically acceptable salt thereof in combination with fluticasone propionate or a physiologically acceptable solvate thereof.

15. A pharmaceutical aerosol formulation according to claim 1 further comprising a particulate medicament, optionally in combination with another particulate medicament, and a fluorocarbon or hydrogen-containing fluorocarbon propellant.

16. A compound which is [(7,7,8,8,8-pentafluorooctyl) oxy] acetic acid or a salt or solvate thereof.

* * * * *